US005631133A

United States Patent [19]
Hanahan et al.

[11] Patent Number: 5,631,133
[45] Date of Patent: May 20, 1997

[54] TRANSITION IN TRANSCRIPTIONAL ACTIVATION BY INTRACELLULAR HORMONE RECEPTORS AT THE TUMOR STAGE OF DERMAL FIBROSARCOMA DEVELOPMENT

[75] Inventors: Douglas Hanahan; Keith R. Yamamoto; Maria d. M. Vivanco, all of San Francisco, Calif.

[73] Assignee: The Regents of the University of California, Oakland, Calif.

[21] Appl. No.: 439,813

[22] Filed: May 12, 1995

[51] Int. Cl.$^6$ .............................. C12Q 1/68; C12P 21/00; C12N 15/65; C12N 5/10

[52] U.S. Cl. .......................... 435/6; 435/69.4; 435/172.1

[58] Field of Search ......................... 435/69.1, 69.4, 435/252.3; 436/64; 536/51

[56] References Cited

U.S. PATENT DOCUMENTS 5,071,773  12/1991  Evans et al. .......................... 436/501
5,506,102  4/1996   McDonnell ............................ 435/6

OTHER PUBLICATIONS

Angel et al. (1987), *Mol. Cell. Biol.,* 7:2256–2266.
Beato (1989), *Cell,* 56:335–344.
Bohen et al. (1993), *Proc. Natl. Acad. Sci. USA,* 90:11424–11428.
Borrow et al. (1990), *Science,* 249:1577–1580.
Bossy–Wetzel et al. (1992), *Genes and Dev.,* 6:2340–2351.
De Th''et al. (1990), *Nature,* 347:558–561.
de Wet et al. (1987), *Mol. Cell. Biol.,* 7:725–737.
Dejean et al. (1986), *Nature,* 322:70–72.
Denis et al. (1992), *J. Steroid Biochem. and Mol. Biol.,* 41:739–745.
Diamond et al. (1990), *Science,* 249:1266–1272.
Doucas et al. (1991), *EMBO J.,* 10:2237–2245.
Droms et al. (1993), *Int. J. Cancer,* 53:1017–1022.
Durst et al. (1989), *Virology,* 173:767–771.
Funder et al. (1988), *Science,* 242:583–585.
Gaub et al. (1990), *Cell,* 63:1267–1276.
Godowski et al. (1987), *Nature,* 325:365–368.
Hashimoto et al. (1984), *Proc. Natl. Acad. Sci. USA,* 81:6637–6641.
Jonat et al. (1990), *Cell,* 62:1189–1204.
Jordan and Morrow (1993), *Stem Cells,* 11:252–262.
Jordan and Murphy (1990), *Endocr. Rev.,* 11:578–610.
Kaspers et al. (1994), *Leukemia and Lymphoma,* 13:187–201.
McKnight and Yamamoto (eds.), (1992) *Transcriptional Regulation,* "Combinatorial Regulation at a Mammalian Composite Response Element," Cold Spring Harbor Lab. Press, New York, 1169–1192.
Miesfeld et al. (1987), *Science,* 236:423–427.
Oikarinen et al. (1993), *J. Invest. Dermatol.,* 101:205–210.
Picard et al. (1987), *EMBO J.,* 6:3333–3340.
Poduslo (1989), *Archiv. Biochem. Biophysics,* 272:318–322.
Qi et al. (1989), *Mol. Endocrinol.,* 3:1279–1288.
Schena and Yamamoto (1988), *Science,* 241:965–967.
Schena et al. (1991), *Proc. Natl. Acad. Sci. USA,* 88:10421–10425.
Schüele et al. (1990), *Cell,* 62:1217–1226.
Smith et al. (1992), *J. Cl. Oncology,* 10:839–864.
Strawhecker and Pelling (1992), *Carcinogenesis,* 13:2075–2080.
Truss and Beato (1993), *Endocr. Rev.,* 14:459–479.
Walsh and Avashia (1992), *Cleveland Clinic J. Med.,* 59:505–515.
Wilding (1992), *Cancer Surv.,* 14:113–130.
Yang et al. (1990), *Cell,* 62:1205–1215.
Yoshinaga and Yamamoto (1991), *Molec. Endocrinol.,* 5:844–853.

*Primary Examiner*—David Guzo
*Assistant Examiner*—William Sandals
*Attorney, Agent, or Firm*—Townsend and Townsend and Crew LLP

[57] ABSTRACT

Intracellular hormone receptors are discovered to undergo posttranslational regulation. Assays to assess cancer progression and to permit discovery of a new class of biologically active compounds are provided. Related kits are also provided.

20 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TCGACTGATC  TCGCCAGAAC  ATCATGTTCT  GCGTCGCCAG  GC                42
```

( 2 ) INFORMATION FOR SEQ ID NO:2:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TCGACTCTAG ACTGAACGGT GACTCAAACT GCCGCTGCAG GC　　　　　　　　　　　　　　42

( 2 ) INFORMATION FOR SEQ ID NO:3:

( i ) SEQUENCE CHARACTERISTICS:
      ( A ) LENGTH: 57 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:3:

TCGACTGATG CCTGTACAGG ATGTTCTAGC TACGAACCCT CGTGAGTCAG TCGAGGC　　　　　　　57

TRANSITION IN TRANSCRIPTIONAL ACTIVATION BY INTRACELLULAR HORMONE RECEPTORS AT THE TUMOR STAGE OF DERMAL FIBROSARCOMA DEVELOPMENT

THE GOVERNMENT HAS CERTAIN RIGHTS IN THIS INVENTION

This invention was made with Government support under Grant Nos. R01 CA45234, P01 DK41822, R37 CA20535, and P01 HL438821, awarded by the National Institutes of Health and Grant No. MCB 9307388, awarded by the National Science Foundation. The Government has certain rights in this invention.

BACKGROUND OF THE INVENTION

In general, molecular analyses of mammalian cell functions, such as gene transcription and its regulation, have been carried out with cells that have suffered neoplastic transformation or have been otherwise converted to continuously dividing, established cell lines. Although much valuable information has been extracted from these experimentally tractable models, it is clear that normal and immortalized cells differ in important ways. Defining and understanding these differences at the molecular level is a goal in understanding normal cell function, and of cancer and other proliferative diseases.

The conversion of a normal cell into a neoplastic cell occurs in multiple steps (Vogelstein and Kinzler (1993) Trends Genet., 9: 138–141). One approach to studying this process employs transgenic mice carrying dominant negative oncogenes or inactivated tumor suppressor genes (Hanahan (1988) Annu. Rev. Genet., 22: 479–519). For example, a small proportion of dermal fibroblasts in mice bearing transgenic bovine papillomavirus type I (BPV-1) genomes proceeds through two histological grades of hyperplasia, termed mild and aggressive fibromatosis, and finally emerges as dermal fibrosarcomas. Cells cultured from each of these stages appear to retain characteristics of the lesions from which they were derived (Sippola-Thiele et al. (1989) Mol. Cell. Biol. 9: 925–934). All three pathological stages contain BPV-1 DNA and RNA transcripts, and the aggressive fibromatosis and fibrosarcoma cells form tumors after inoculation into mice. Importantly, the aggressive fibromatosis and fibrosarcoma cultures contain similar levels of the BPV-1 E5 and E6 oncogene products (Sippola-Thiele et al., Supra). Thus, the BPV-1 transgene is not a sufficient determinant of the dermal fibrosarcoma phenotype, suggesting that changes in cellular components must contribute to the conversion of the advanced hyperplasia into fibrosarcoma.

Fibrosarcomas contain one or both of two karyotypic defects, neither of which is seen in the fibromatosis stages: translocations involving chromosome 14 (60%), or duplications of chromosome 8 (70%); about 30% of the tumors carry both lesions (Lindgren et al., (1989) Proc. Natl Acad. Sci. USA 86:5025–5029). It is apparent that sites of consistent chromosome rearrangements can localize genes that may be critically involved in malignant transformation, and that the rearrangements themselves can subvert the normal functioning of these genes (Bishop (1991) Cell, 64:235–248; Solomon et al., (1991) Science, 254:1153–1160; Marshall (1991) Cell, 64:313–326). In this regard, it seemed potentially interesting that a proto-oncogene, JunB, was found to reside within a region of chromosome 8 (Mattei et al. (1990) Oncogene, 5: 151–156) that is most commonly duplicated in fibrosarcomas (Lindgren et al., Supra). A survey of several members of the AP-1 factor family (Vogt et al. (1990) Adv. Cancer Res., 55: 1–35; Hunter et al. (1991) Cell, 64:249–270; Hunter and Karin (1992) Cell, 70:375–387; Kerppola and Curran (1991) Science, 254:1210–1214) during the progression to fibrosarcoma revealed that JuneB and c-Jun were elevated in the aggressive fibromatosis as well as fibrosarcoma cultures, whereas JunD and c-Fos remained constant (Bossy-Wetzel et al. (1992) Genes and Dev., 6:2340–2351). However, overexpression of JuneB and/or c-Jun was not sufficient to induce the complete tumor cell phenotype; mild fibromatosis cells overexpressing either or both of these genes displayed anchorage-independent growth in soft agar, but failed to produce tumors upon inoculation into histocompatible mice. Thus, it appears that additional events during tumor progression distinguish aggressive fibromatoses from fibrosarcomas.

Extensive interactions have been described between AP-1 factors and various members of the "intracellular receptor" super family, including the estrogen receptor (ER) (Gaub et al. (1990) Cell, 63:1267–1276; Doucas et al. (1991), EMBO J., 10:2237–2245), the retinoic acid (RAR) and vitamin D (VDR) receptors (Schüele et al. (1990a) Cell 61:497–504; Schüele et al. (1990b) Cell, 62:1217–1226), and especially the glucocorticoid receptor (GR) (Diamond et al. (1990) Science, 249: 1266–1272; Jonat et al. (1990) Cell 62:1189–1204; Schüele et al, (1990b)Supra; Yang et aL (1990) Cell, 62: 1205–1215). The intracellular receptors mediate the effects of various small ligands, including steroids, thyroid hormone, retinoids and vitamin D (for reviews see Evans (1988) Science, 240:889–895; Ham and Parker (1989) Curr. Opin. Cell Biol., 1:503–511; Burnstein et al. (1989), Ann. Rev. Physiol., 51:683–699; Truss and Beato (1993) Endocr. Rev., 14:459–479). Although distinct in detail, these receptors share general characteristics of structure and mode of action. Thus, the GR binds its cognate hormone in the cytoplasm, migrates to the nucleus and regulates transcription upon association with specific glucocorticoid response element (GRE) DNA sequences near target genes. Two broad classes of GREs have been described: GR binding at "simple GREs", which contain imperfect palindromes of hexamer half-sites separated by three base pairs (Beato (1989) Cell, 56:335–344), is sufficient for enhancement of transcription from nearby promoters, although repression has not been observed from such sites. In contrast, GR acts only in collaboration with other factors that bind at "composite GRE" sites that lack a common consensus sequence; at these sites, GR can either enhance or repress transcription (Yamamoto et al., (1992) In McKnight and Yamamoto (eds.) Transcriptional regulation Cold Spring Harbor Lab. Press, New York, 1169–1192).

Steroid hormones are essential regulators of normal cell growth, differentiation and homeostasis (for review see Walsh and Avashia (1992) Cleveland Clinic J. Med. 59:505–515). For example, estrogens and androgens can function as powerful mitogens while also playing critical roles in differentiation (Jordan and Morrow (1993) Stem Cells 11:252–262; Wilding (1992) Cancer Surv. 14:113–130), whereas glucocorticoids tend to promote differentiation and inhibit proliferation. Steroids are also commonly used therapeutics. Thus, topical glucocorticoids reduce tissue destruction in certain skin disorders by down-regulating type IV collagenase (Oikarinen et al., (1993) J. Invest. Dermatol. 101:205–210). Intracellular receptors and their ligands have been also implicated in various malignancies. For example, the RARβ gene can be rearranged as a result of hepatitis B virus integration in certain human hepatocellular carcinomas (Dejean et al. (1986) *Nature*, 322:70–72), and RARα is split into two chimeric proteins by a t(15:17) translocation in acute promyelocyfic leukemia (De Thé et al. (1990) *Nature*, 347:558–561; Borrow et al. (1990) *Science*, 249:1577–1580).

Estrogens promote the course of several cancers (Jordan and Murphy (1990) *Endocr. Rev.*, 11:578–610). Glucocorticoids inhibit the growth of carcinogen-induced tumors in mouse lung (Droms et al. (1993), *Int. J. Cancer*, 53: 1017–1022), mouse skin (Strawhecker and Pelling (1992) *Carcinogenesis*, 13:2075–2080) and rat colon (Denis et al. (1992), *J. Steroid Blochem. and Mol. Biol.*, 41:739–745). In contrast, glucocorticoids markedly enhance the transformation of cultured human epithelial cells by Kirsten murine sarcoma virus (KMSV) (Durst et al. (1989) *Virology*, 173:767–771), and strongly activate mouse mammary tumor virus gene transcription and virus production (Truss and Beato (1993) Supra).

The present invention demonstrates for the first time that the activity of intracellular hormones differs between normal and immortalized cells, explaining various aspects of the functional interactions of intracellular receptors with AP1, in addition to the effects of steroids and retinoids on cell growth and differentiation.

SUMMARY OF THE INVENTION

We have discovered that normal cells and pre-cancerous cells have a heretofore unrecognized capability to post-translationally limit the magnitude of gene expression induced by intracellular hormone receptors, relative to cancerous and immortal cells. This discovery allows normal cells, pre-cancerous cells and immortal cells to be distinguished on the basis of the relative transcriptional activity of an intracellular hormone receptor in the various cell types. The discovery that intracellular hormone receptors are post-translationally regulated also provides for the screening of compounds which specifically affect the post-translational regulation of the intracellular hormone receptor.

Accordingly, the present invention provides a variety of assays for the detection of post translational intracellular gene regulation, including assays for the detection of compounds which inhibit or enhance the level of activity of an intracellular hormone receptor. These assays and corresponding kits are useful in a variety of contexts, including the detection of cancer, assessment of the stage of a cancer, and commercially important drug discovery techniques.

In one set of preferred embodiments, the invention provides assays for detecting post-translational regulation of an intracellular hormone receptor in the presence of a cognate hormone. The assay monitors the expression of a marker gene expressed by an expression cassette from a promoter that includes a DNA binding site for the intracellular receptor. The expression cassette is transfected into a first eukaryotic cell such as a normal mammalian human skin cell and an immortal eukaryotic cell, such as a transformed mammalian skin cell. The cells express the intracellular hormone receptor in a non rate limiting amount. The cells are then contacted with the cognate hormone and the level of expression of the marker gene is monitored and compared in the first cell and the immortal cell.

The embodiment optionally includes methods of determining whether a cell of interest (a "test" cell) displays a normal or transformed intracellular hormone activity phenotype. The activity of an intracellular hormone in the test cell is compared to the first eukaryotic cell and the immortal cell by transfecting the test cell with the marker gene expression cassette described in the first portion of the embodiment, contacting the test cell with the cognate hormone and comparing the level of expression of the marker gene in the test cell to the first eukaryotic cell and the immortal cell. Depending on the selection of the first eukaryotic cell, the immortal cell and the test cell, it is possible to determine the intracellular hormone receptor phenotype of the test ceil. For instance, where the first eukaryotic cell is an early stage or pre-cancerous skin cell and the immortal cell is a transformed cell or is derived from a late-stage skin cell malignahoy, the test cell can be assigned as being derived from either an early or late stage malignancy.

In order to express intracellular hormone in the first eukaryotic cell, the immortal cell or the test cell in a non rate limiting amount, it is sometimes necessary to transfect (transiently or permanently) one or all of the cells with a recombinant expression cassette which expresses the intracellular hormone receptor. Typically, expression of the intracellular hormone receptor by the expression cassette is directed by an inducible or constitutive promoter.

In preferred embodiments, the assays also provide methods of screening for bioactive compounds which activate the intracellular hormone receptor. For instance, in one preferred embodiment a test cell is transfected with the marker gene expression cassette described above, contacted with a non rate limiting amount of cognate hormone, and the level of expression of the marker gene assessed. The test cell is then contacted with a biologically active compound, and the level of expression of the marker gene compared to the level of marker gene expression prior to contacting the cell with the biologically active compound. Typically, the first eukaryotic cell and the immortal cell described above are examined by the procedures outlined above in conjunction with the test cell as a control to establish that the activation of the intracellular hormone receptor by the bioactive compound occurs post-translationally. Typically, the test cell, first eukaryotic cell and the immortal cell are transfected with an expression cassette comprising a nucleic acid encoding the intracellular hormone receptor, often under the control of an inducible or consritutive promoter. The intracellular expression cassette ensures that the level of intracellular hormone receptor in the cell of interest is present in a non rate limiting amount.

In a second set of preferred embodiments, the present invention provides assays for detecting the post-translational regulation (activation or inhibition) of an intracellular receptor in the presence of a cognate hormone. The assay utilizes two expression cassettes. The first expression cassette includes a nucleie acid encoding the intracellular hormone receptor operably linked to a first promoter. The second expression cassette includes a marker gene operably linked to a second promoter having a response element for the intracellular hormone receptor. Typically, the response element is not located close to the start-site of transcription (i.e., within 50 base pairs of the start site), but, as with many enhancer elements, the precise location of the response element is not critical. The two expression cassettes are co-transfected into a primary cell (or cell population) and a second cell (or cell population). The transfected cells are separately contacted with the cognate hormone and the level of expression of the marker gene in the two cells or cell populations is measured and compared. Thus, the assay allows for a comparison of the relative level of activity of the intracellular hormone receptor in different cell types. This is particularly useful where the intracellular hormone receptor activity level of one of the cell types is characterized, because it allows for a simple determination of the level of intracellular hormone receptor activity in the second cell population. For instance, where the first cell type is a normal cell, e.g., obtained from a sample of normal human skin and grown in culture without serial passage in culture, comparison of the level of marker gene expression between the first cell type and the second cell type provides a measure of whether the second cell type is normal, or, e.g., malignant. Similar information is obtained where the first cell type is a transformed cell which displays an activated intracellular hormone receptor phenotype.

The assay is further refined by providing an additional measure of the level of activity of the intracellular hormone receptor. For instance, where the primary cell is a normal or pre-cancerous cell, a third immortal cell is used with the assay. The third cell is co-transfected with the same expression cassettes as the primary and second cell, and the level of expression of the marker gene in all three cell types is compared. By providing two known cell phenotypes in the assay (i.e., the primary and immortal cells), it is possible to assess which phenotype the second cell most nearly matches. For instance, where the primary cell is a normal human skin cell the second cell is a human skin cell and the immortalized cell line is an immortalized skin cell line, comparison of the second cell provides a measure of whether the second human skin cell is a cancerous cell, and of the stage of malignancy. For instance, an activated intracellular hormone receptor cell phenotype is typically an indication that the cell is an end-stage cancer.

In a third set of embodiments, assays for identifying compounds which differentially modulate the activity of an intracellular hormone receptor are provided. The assay takes advantage of the discovery presented herein that the intracellular hormone receptor is differentially active in normal versus cancerous cell types. In the assay, a primary cell, which expresses the intracellular hormone in a non rate limiting amount, and an immortal cell are transfected with an expression cassette which includes a marker gene operably linked to a promoter with an intmcellular hormone response element. The cells are contacted with a non rate limiting amount of cognate hormone and the level of expression of the marker gene in the two cell types is measured and compared. The cells are then contacted with a compound of interest and the level of expression of the marker gene in the two cell types is again measured and compared. The compound is said to modulate the activity of the intracellular hormone receptor when the compound differentially affects the level of marker gene expression from either the primary cell or the immortal cell.

In preferred embodiments, the primary cell and the immortal cell are transfected with an expression cassette which includes a nucleic acid encoding the intracellular hormone receptor to ensure that the level of hormone receptor is non rate limiting.

The present invention also provides kits for the detection of intracellular hormone receptor activity. Typically, the kits include a container and an expression cassette encoding a marker gene operably linked to a promoter with an intracellular hormone response element. The promoter is designed to alter the expression of the marker gene upon binding of the intracellular hormone receptor response element to an intracellular hormone receptor. The kits optionally include, for example, any of the following: a second expression cassette which encodes an intracellular hormone receptor, an immortal cell line, normal cells, reagents, buffers, marker gene detection equipment, and instructional materials.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of illustrating the present invention, the following terms are defined more explicitly below.

An "antibody" is a polypeptide substantially encoded by an immunoglobulin gene or immunoglobulin genes, or fragments thereof which specifically bind and recognize an analyte (antigen). Recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classess, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist e.g., as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially an Fab with part of the hinge region (see, *Fundamental Immunology, Third Edition*, W. E. Paul, ed., Raven Press, New York (1993), which is incorporated herein by reference, for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

A "cognate hormone" as a biologically active molecule which interacts with an intracellular hormone receptor, typically causing the intracellular hormone receptor to become able to bind to an intracellular hormone response element. The term "cognate hormone" as used herein includes an intracellular hormone receptor's natural biological hormone. For instance, retinoic acid is a cognate hormone to the retinoic acid receptor; estrogen is a cognate hormone to the estrogen receptor; vitamin D is a cognate hormone to the vitamin D receptor. The term cognate hormone also refers to synthetic hormones which have similar functional properties. For instance, the synthetic glucocorticoid dexamethasone is a cognate hormone to the glucocorticoid receptor.

An "intracellular hormone receptor" is distinguished by its general mode of action. An intracellular hormone receptor binds its cognate hormone in the cytoplasm, and migrates to the nucleus, or binds its hormone in the nucleus directly. The intracellular hormone receptor then regulates the transcription of genes, typically upon binding of the hormone receptor to the relevant hormone receptor binding site.

An "intracellular hormone receptor DNA binding site" or an "intracellular hormone receptor response element" is an enhacer or repressor binding site in a gene for an intracellular hormone receptor. Often the intracellular hormone DNA binding site has a particular consensus sequence which permits the intracellular hormone receptor to bind at the DNA binding site. However, more complex interactions also are encompassed within the meaning of this definition, wherein the interaction of the intracellular hormone receptor to the intracellular hormone receptor DNA binding site is mediated by additional factors, and the intracellular hormone receptor DNA binding site does not have a sequence which matches any particular consensus sequence. For instance, two broad classess of intracellular hormone receptor DNA binding sites have been described for the Glucocorticoid receptor (GR). GR binds to simple GR elements (GREs) which contain imperfect palindrome hexamer half-sites separated by three base pairs. The described GREs provide transcriptional activation of a gene upon binding of the GR. In contrast, GR acts in collaboration with other factors that bind "composite GRE" sites. These composite GRE sites lack a common consensus sequence, and may act as repressors or activators of genes.

An "immunoassay" is an assay that utilizes an antibody to specifically bind an analyte. The immunoassay is characterized by the use of specific binding properties of a particular antibody to isolate, target, and/or quantify the analyte.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

The term "nucleic acid probe" refers to a molecule which binds to a specific sequence or subsequence of a nucleic acid. A probe is preferably a nucleic acid which binds through complementary base pairing to the full sequence or to a subsequence of a target nucleic acid. It will be understood by one of skill in the art that probes may bind target sequences lacking complete complementarity with the probe sequence depending upon the stringency of the hybridization conditions. The probes are preferably directly labelled as with isotopes, chromophores, lumiphores, chromogens, or indirectly labelled such as with biotin to which a streptavidin complex may later bind. By assaying for the presence or absence of the probe, one can detect the presence or absence of the select sequence or subsequence.

A "marker gene" is a nucleic acid which is detectable, or provides for the synthesis of a detectable product. For instance, the marker gene can encode a nucleic acid which is detected by hybridization to a probe. Alternatively the marker gene can encode a protein which is detectable, e.g., through interaction with an antibody. The marker gene can also encode a protein such as chloramphenicol transferase which catalytically alters a detectable marker. A marker gene can also confer viability to a cell grown in specialized media, thereby providing an indication of the level of expression of the marker gene.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, dioxigenin, or haptens and proteins for which antisera or monoclonal antibodies are available.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. The promoter also includes distal enhancer or repressor elements which can be located as much as several thousand base pairs from the start site of transcription. Thus, a promoter which includes an intracellular hormone receptor DNA binding site optionally locates the intracellular hormone receptor DNA binding site distal to the start site of transcription. A "constitutive" promoter is a promoter which is active under most environmental conditions and states of development or cell differentiation. An "inducible" promoter responds to an extracellular stimulus.

The term "recombinant" when used with reference to a cell indicates that the cell encodes a DNA whose origin is exogenous to the cell-type. Thus, for example, recombinant cells express genes that are not found within the native (non-recombinant) form of the cell.

A "recombinant expression cassette" is a nucleic acid construct, generated recombinantly or synthetically, with a series of specified nueleic acid elements which permit transcription of a particular nucleic acid. The recombinant expression cassette can be part of a plasmid, virus, or nueleic acid fragment. Typically, the recombinant expression cassette includes a nucleic acid to be transcribed, and a promoter. In some embodiments, the expression cassette also includes, e.g., an origin of replication, and/or chromosome integration elements.

The phrases "specifically binds to a protein" or "specifically hybridizes to" or "specifically immunoreactive with", when referring to an antibody refers to a binding reaction which is determinative of the presence of the protein in the presence of a heterogeneous population of proteins and other biologics. Thus, under designated assay conditions, antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

DETAILED DESCRIPTION

The present invention stems from the discovery that intracellular hormone receptors are post-translationally regulated. Intracellular hormone receptors show different activity phenotypes in transformed versus normal cells, even when the receptor and corresponding hormone are present in equivalent amounts. This discovery provides one of skill with a variety of commercially useful assays and related kits. These assays are useful in the detection of cancer and in the assessment of the stage of cancers. The assays also provide commercially useful drug discovery methods.

Assays

The present invention provides several assays for the detection of cancer, assessment of the relative stage of a cancer, and drug screening assays which measure the effect of a compound on the activity of an inncellular hormone receptor, in normal cells, early-stage cancers and end-stage aggressive malignancies.

Typically, the assays measure the level of intracellular hormone receptor activity in normal and/or early-stage cancers and immortal cells and/or end-stage malignancies, providing a measure of the intracellular hormone receptor activity phenotype. Comparing the level of intracellular receptor activity in normal cells and immortal cells provides a measure of the difference in the activity phenotypes in the two cell types. The activity phenotype of the intracellular hormone receptor in any cell type can then be identified by comparison to the normal and immortal activity phenotypes.

The activity phenotype which is measured is not dependent on the level of intracellular hormone or intracellular hormone receptor. As described herein, normal cells and immortal cells have different transcriptional activity levels for intracellular hormone receptors, even when the level of hormone and hormone receptor is the same in the two cell types. Thus, the present invention provides for commercially useful compound screening assays which assess whether a compound has a differential effect on the activity phenotype of normal and immortal cells. Previously, no investigator would have tested the ability of a compound to differentially affect the activity phenotypes of normal and immortal cells, because it was not known that the two cell types had different activity phenotypes.

Typically, the level of expression of a promoter which includes an intracellular hormone response element is measured in the cell types which are to be tested. Ordinarily, this is performed by monitoring the amount of marker gene transcript produced under the control of the promoter which includes an intracellular hormone response element. This is done either by measuring the level of transcript produced under the control of the promoter, or by measuring the amount of transcript which is translated into a polypeptide. One of skill will recognize that virtually any gene may be adapted for use in detecting the level of expression directed by the promoter, and that a wide variety of minimal promoters suitable for use in conjunction with intracellular response element are known. One of skill is able to select appropriate detectable marker genes and promoters, depending on the cell type into which an expression cassette containing the construct is to be transfected.

Expression Cassettes

The assays of the present invention utilize two general types of expression cassettes. The first type of expression cassette has a marker gene under the control of a promoter which includes an intracellular hormone receptor response element (IHRRE). A wide variety of IHRREs are well characterized in the art, including the estrogen response element (ERE), the glucocorticoid response element (GRE) the retinoic acid response element (RARE), and the vitamin D response element (VDRE) (See, Beato et al. (1989); Burnstein et al (1989); Dejan et al. (1986); De The et al. (1990) Diamond et al. (1990) Evans et al. (1988); Ham and Parker (1989), and Yamamoto et al. (1992) all supra). As described below, the marker gene can be essentially any known gene. Detection of the marker gene is accomplished by detecting the marker gene transcript, the polypeptide encoded by the marker gene, or product of the polypeptide (e.g., detectable enzymatic digestion product).

The second type of expression cassette encodes an intracellular hormone receptor under the control of a promoter. Typically, the cassette is used where the level of intracellular hormone receptor produced from the expression cassette in the transfected cell is non rate limiting. Accordingly, the expression cassette promoter is ordinarily a strong promoter which directs high levels of intracellular hormone receptor nucleic acid transcript. The particular promoter used with this type of expression cassette is not critical, and is either inducible or constiitutive (See, Ausbel, supra and Sambrook, supra for examples of appropriate strong promoters). The particular promoter to be used depends upon the cell into which the cassette is to be transfected. Examples of useful promoters in yeast include GAL1,10 (Johnson and Davies (1984) *Mol. and Cell. Biol.* 4: 1440–1448) ADH2 (Russell et al. (1983) *J. Biol. Chem.* 258:2674–2682), PHO5 (*EMBO J.* 6:675–680, 1982), and MFαl (Herskowitz and Oshima (1982) in *The Molecular Biology of the Yeast Saccharomyces* eds. Strathern et al. Cold Spring Harbor Lab., Cold Spring Harbor, N.Y., pp. 181–209). When the host cell is of animal origin, illustrative expression control sequences for construction of the promoter are obtained from the rous sarcoma virus promoter (See, Ausbel, supra and Sambrook, supra) SV-40 promoter (*Science,* 222:524–527, 1983), the CMV I. E. Promoter (*Proc. Natl. Acad. Sci.* (1984) 81:659–663) or the metallothionein promoter (*Nature* (1982) 296:39–42).

In addition to a promoter sequence, the expression cassettes typically contain a transcription termination region downstream of the gene of interest to provide for efficient termination. The termination region may be obtained from the same gene as the promoter sequence or may be obtained from different genes. Polyadenylation sequences are also commonly added to the expression cassette (Albert and Kawasaki (1982) *Mol. and Appl. Genet* 1:419–434).

The expression cassettes may also comprise sequences permitting replication of the plasmid in both eukaryotes and prokaryotes, i.e., shuffle vectors, and selection markers for both prokaryotic and eukaryotic systems (See, Sambrook, supra). Methods of recombinantly constructing appropriate expression cassettes are well known in the art. Sambrook, supra and Ausbel, supra provide one of skill with a general guide to recombinant technology.

Transfection of Eukaryotic Cells

Eukaryotic cells are competent or rendered competent for transfection of the expression cassettes of the invention by various means known to persons of skill. For instance, there are several well-known methods of introducing nucleic acids into animal cells. These include: calcium phosphate precipitation, fusion of the recipient cells with bacterial protoplasts containing the nucleic acid, treatment of the recipient cells with liposomes containing the nucleic acid, DEAE dextran, electroporation and micro-injection of the nucleic acid directly into the cells.

Culture of Cells

The culture of cells used in the assays of the present invention, including cell lines and cultured cells from tissue samples is well known in the art. Freshney (*Culture of Animal Cells a Manual of Basic Technique*, third edition Wiley-Liss, New York (1994)) provides a general guide to the culture of cells.

Briefly, when culturing cells from a tissue sample, a primary culture is obtained by allowing the cells to migrate out of the tissue onto a suitable substrate, or by desegregating the cells in the tissue sample enzymatically or mechanically and allowing the cells to attach to the substrate. In the case of untransformed cells, a flat substrate typically permits maximum proliferation.

Once the primary culture has proliferated across the substrate, the primary culture is sub-cultured, giving rise to a secondary culture. As the primary culture is subcultured (or "transferred," or "passaged") it becomes known as a cell line. For purposes of this invention, normal cells typically include cells isolated from a tissue and the primary culture. However, because cells lose heterogeneity and take on abnormal characteristic upon serial passage in culture, the preferred "normal" cell in the assays of the present invention has undergone only limited serial passage (less than 3 passages in culture).

Detection of Marker Gene Transcript

Cloning, PCR, LCR, TAS, 3SR, and QB Amplification

The present invention is used in conjunction with techniques such as PCR, TAS, 3SR, QB amplification and cloning, to amplify and detect a nucleic acid in a biological sample which encodes a marker gene.

The level of expression of marker gene transcript from the expression cassettes described herein, e.g., which include an intracellular receptor response element, provides a measurement of the level of transcriptional activity of the corresponding intracellular hormone receptor. The level of marker gene expression is determined in vitro or in situ, e.g., by measurement of the level of corresponding RNA transcript.

Typically, nucleic acids which bind to the marker gene transcript (i.e., marker gene probes) are cloned, or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). The marker gene probes are then hybridized to marker gene message to determine the level of marker gene expression, e.g., by northern analysis, or by in situ hybridization.

Alternatively, the marker gene transcript is directly quantitated, or amplified as described above and then quantitated, typically by mobility of the transcript or amplified transcript through a gel, e.g., in conjunction with ethidium bromide staining, or through spectrophotometric or spectroscopic techniques.

A wide variety of detection, cloning and in vitro amplification methods suitable for the detection of marker gene transcript are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et at., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; and Barfinger et al. (1990) Gene 89, 117. The level of transcript can also be measured by monitoring the binding of an antibody specific for the transcript as described for translation products below.

Detection of Marker Gene Peptides

The assays of the present invention typically test the level of transcriptional activity directed by a promoter which includes an intracellular hormone response element. As noted above, in one set of embodiments, the level of transcript produced from the promoter is measured by quantitating the transcript. In a second set of embodiments, the level of transcriptional activity is measured by quantitating the polypeptide translated from the marker gene transcript. Typically, the transcript encodes a protein which is detectable by techniques well known to persons of skill. In one set of preferred embodiments, the marker gene encodes an enzyme which catalyzes a detectable reaction, thereby providing a measure of the amount of marker gene polypeptide present in a cell or population of cells. Examples of such enzymes which are well-known to persons of skill include β-galactosidase (particularly the LacZ fragment), alcohol dehydrogenase, chloramphenicol transferase and HIS3. Selectable marker genes which confer viability to cells upon expression in a particular environment can also be used to assess the level of marker gene transcript. Examples of well-known selectable markers include aminoglycoside phosphotransferase (APH), dihydrofoliate reductase (DHFR), hygromycin-B-phosphotransferase (HPH), thymidine kinase (TK), xanthine-guanine phosphoribosyltransferase (XGPRT) and adenosine deaminase (ADA) Luciferase.

Although marker genes which catalyze a detectable reaction are a preferred form of detecting the level of transcriptional activity for a promoter in a particular cell, one of skill will recognize that virtually any gene can serve as a marker gene by measuring the level of marker gene polypeptide directly. This is performed either by separating the protein from other cellular components and quantitating it, or by using a detectable binding agent such as an antibody which binds the marker gene specifically.

Antibodies to Marker Gene Polypeptides

One preferred method of detecting a marker gene polypeptide is to use an antibody coupled to a detection system. A variety of polypeptides have well characterized antibodies, making them suitable marker gene polypeptides. However, virtually any gene can be used as a marker gene by generating an antibody to the encoded polypeptide, which is then used in the assay.

a. Antibody Production

A number of immunogens are used to produce antibodies specifically reactive with the marker gene polypeptide. Recombinant or synthetic polypeptides of 10 amino acids in length, or greater, selected from sub-sequences of a marker gene polypeptide are the preferred polypeptide immunogen for the production of monoclonal or polyclonal antibodies against the marker gene.

Recombinant polypeptide immunogens are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen, preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high liters of antibody to the immunogen are obtained, blood is collected from the animal and antisera are prepared. Further fractionation of the antisera to enrich for antibodies reactive to the polypeptide is performed where desired. See, e.g., Coligan (1991) *Current Protocols in Immunology* Wiley/Greene, New York; and Harlow and Lane (1989) *Antibodies: A Laboratory Manual* Cold Spring Harbor Press, New York, which are incorporated herein by reference, and the examples below.

In some instances, it is desirable to prepare monoclonal antibodies from various mammalian hosts, such as mice, rodents, primates, humans, etc. Description of techniques for preparing such toonotional antibodies are found in, e.g., Stites et aL (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimetic antibodies such as humanized murine antibodies.

Other suitable techniques involve selection of libraries of recombinant antibodies in phage or similar vectors. See, Huse et al. (1989) *Science* 246: 1275–1281; and Ward, et al. (1989) *Nature* 341: 544–546. Specific monoclonal and polyclonal antibodies will usually bind with a $K_D$ of at least about 0.1 mM, more usually at least about 1 µM, and most preferably at least about 0.1 µM or better.

Frequently, the polypeptides and antibodies will be labeled by joining, either covalently or non covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The antibodies of this invention are also used for affinity chromatography in isolating and quantitating marker gene polypeptides. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified marker gene polypeptides are released.

b. Immunoassays

A particular protein can be quantified by a variety of immunoassay methods. For a review of immunological and immunoassay procedures in general, see Stites and Terr (eds.) 1991 *Basic and Clinical Immunology* (7th ed.). Moreover, the immunoassays of the present invention can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, New York; and Ngo (ed.) (1988) *Non isotopic Immunoassays* Plenum Press, New York.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled marker gene peptide or a labeled anti-marker gene antibody. Alternatively, the labeling agent may be a third moiety, such as another antibody, that specifically binds to the antibody/ marker gene complex, or to a modified capture group (e.g., biotin) which is covalently linked to the marker gene peptide or anti-marker gene antibody.

In a preferred embodiment, the labeling agent is an antibody that specifically binds to the capture agent (anti-marker gene antibody). Such agents are well known to those of skill in the art, and most typically comprise labeled antibodies that specifically bind antibodies of the particular animal species from which the capture agent is derived (e.g., an anti-idiotypic antibody). Thus, for example, where the capture agent is a mouse derived anti-marker gene antibody, the label agent may be a goat anti-mouse IgG, i.e., an antibody specific to the constant region of the mouse antibody.

Other proteins capable of specifically binding immunoglobulin constant regions, such as streptococcal protein A or protein G are also used as the labeling agent. These proteins are normal constituents of the cell walls of streptococcal bacteria. They exhibit a strong non immunogenic reactivity with immunoglobulin constant regions from a variety of species. See, generally Kronval, et at., (1973) *J. Immunol.*, 111:1401–1406, and Akerstrom, et at., (1985) *J. Immunol.*, 135:2589–2542.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays are carried out at ambient temperature, although they can be conducted over a range of temperatures, such as 5° C. to 45° C.

(i) Non Competitive Assay Formats

Immunoassays for detecting a marker gene may be either competitive or noncompetitive. Noncompetitive immunoassays are assays in which the amount of captured analyte (in this case, the marker gene) is directly measured. In one preferred "sandwich" assay, for example, the capture agent (e.g., anti-marker gene antibodies) are bound directly to a solid substrate where they are immobilized. These immobilized antibodies then capture marker gene present in the test sample. The marker gene thus immobilized is then bound by a labeling agent, such as a second human marker gene antibody bearing a label. Alternatively, the second marker gene antibody may lack a label, but it may, in turn, be bound by a labeled third antibody specific to antibodies of the species from which the second antibody is derived.

Sandwich assays for a marker gene may be constructed. As described above, the immobilized anti-marker gene specifically binds to the marker gene present in the sample. The labeled anti-marker gene antibody then binds to the already bound marker gene. Free labeled anti-marker gene is washed away and the remaining bound labeled anti-marker gene antibody is detected (e.g., using a gamma detector where the label is radioactive).

(ii) Competitive Assay Formats

In competitive assays, the amount of analyte (e.g., marker gene polypeptide) present in the sample is measured indirectly by measuring the amount of an added (exogenous) analyte displaced (or competed away) from a capture agent (e.g., anti-marker gene antibody) by the analyte present in the sample. In one competitive assay, a known amount of analyte is added to the sample and the sample is contacted with a capture agent, in this case an antibody that specifically binds the analyte. The amount of analyte bound to the antibody is inversely proportional to the concentration of analyte present in the sample.

In a preferred embodiment, the capture agent is immobilized on a solid substrate. The amount of marker gene polypeptide bound to the capture agent is determined either by measuring the amount of marker gene present in an a marker gene/antibody complex, or alternatively by measuring the amount of remaining uncomplexed marker gene. The amount of marker gene polypeptide in a sample to be assayed may also be detected by providing exogenous labeled marker gene to the assay.

A hapten inhibition assay is another preferred competitive assay. In this assay, a known analyte, in this case a marker gene, is immobilized on a solid substrate. A known amount of anti-marker gene antibody is added to the sample, and the sample is then contacted with the immobilized marker gene polypeptide. In this case, the amount of anti-marker gene antibody bound to the immobilized marker gene polypeptide is proportional to the amount of marker gene polypeptide present in the sample. Again the amount of immobilized antibody is detected by quantitating either the immobilized fraction of antibody or the fraction of the antibody that remains in solution. Detection may be direct where the antibody is labeled, or indirect where a labeled moiety is subsequently added which specifically binds to the antibody as described above.

Assays for Marker Genes

A. Sample Collection and Processing

A marker gene transcript or polypeptide is preferably quantified in a biological sample, such as a cell, or a tissue sample derived from a patient. In a preferred embodiment, a marker gene product is quantified in skin cells derived normal or malignant skin cells. Although the sample is typically taken from a human patient, the assays can be used to detect marker gene products in cells from eukaryotes in general, including plants, vertebrates and invertebrates, and in mammals in particular, such as dogs, cats, sheep, cattle and pigs, and most particularly primates such as humans, chimpanzees, gorillas, macaques, and baboons, and rodents such as mice, rats, and guinea pigs.

The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

B. Quantification of Marker Gene Products

Marker gene products may be detected and quantified by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

C. Reduction of Non Specific Binding

One of skill will appreciate that it is often desirable to reduce non specific binding in immunoassays and during analyte purification. Where the assay involves an antigen, antibody, or other capture agent immobilized on a solid substrate, it is desirable to minimize the amount of non specific binding to the substrate. Means of reducing such non specific binding are well known to those of skill in the art. Typically, this involves coating the substrate with a proteinaceous composition. In particular, protein compositions such as bovine serum albumin (BSA), nonfat powdered milk, and gelatin are widely used.

D. Other Assay Formats

Western blot analysis can also be used to detect and quantify the presence of a marker gene product (peptide, transcript, or enzymatic digestion product) in the sample. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a marker gene polypeptide. The anti-marker gene antibodies specifically bind to a marker gene product on the solid support. These antibodies may be directly labeled or alternatively may be subsequently detected using labeled antibodies (e.g., labeled sheep anti-mouse antibodies where the antibody to a marker gene is a murine antibody) that specifically bind to the anti-marker gene antibody.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34–41), which is incorporated herein by reference.

E. Labels

The labeling agent can be, e.g., a monoclonal antibody, a polyclonal antibody, a marker gene binding protein or complex such as those described herein, or a polymer such as an affinity matrix, carbohydrate or lipid. Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., $^3$H, $^{125}$I $^{35}$S, $^{14}$C, or $^{32}$P), enzymes (e.g., LacZ, CAT, horse radish peroxidase, alkaline phosphatase and others, commonly used as detectable enzymes, either as marker gene products or in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

F. Substrates

As mentioned above, depending upon the assay, various components, including the antigen, target antibody, or anti-human antibody, may be bound to a solid surface. Many methods for iramobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glassess, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as rextrans, polyalkylene glycols or suffactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, *J. Biol. Chem.* 245 3059 (1970) which are incorporated herein by reference.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a leetin such as Concanavalin A will bind a carbohydrate containing compound but not a labeled protein that lacks glycosylation. Various solid surfaces for use in noncovalent attachment of assay components are reviewed in U.S. Patent Nos. 4,447,576 and 4,254,082, which are incorporated herein by reference.

Assay Utility

As described herein, the assays of the present invention can be used to detect cancer cells. One discovery presented in this invention demonstrates that intracellular hormone receptors have different activity phenotypes in normal and aggressive cancer cells. Accordingly, the assays of the invention are useful in the determination that a particular cell has an aggressive activity phenotype, and therefore that the cell is an aggressive cancerous cell type. Moreover, the present invention demonstrates that early-stage cancers have a lower intracellular hormone receptor activity phenotype than late-stage aggressive cancers. Therefore, the assays of the present invention are useful in distinguishing aggressive cancers from non aggressive cancers.

By showing that immortal cells and normal cells have different intracellular activity phenotypes, the present invention provides a new target for potential therapeutic agents directed towards modifying this phenotype. For instance, altering a normal cell towards a high activity phenotype would be expected to promote wound healing, while altering a high activity phenotype such as a malignancy towards a low activity phenotype would inhibit metastasis. Accordingly, an assay which detects such activity in compounds is of commercial value to companies involved in the business of drug discovery.

Kits which provide materials to perform the assays of the present invention are useful in the performance of the assays of the invention. Typically, the kits include a container and an expression cassette encoding a marker gene operably linked to a promoter with an intracellular hormone response element. The promoter is designed to alter the expression of the marker gene upon binding of the intracellular hormone receptor response element to an intracellular hormone receptor. The kits optionally include, for example, any of the following: a second expression cassette which encodes an intracellular hormone receptor, an immortal cell line, normal cells, reagents, buffers, marker gene detection equipment, and instructional materials.

A dramatic increase in GR activity at the final stage of dermal fibrosarcoma development Tumorigenesis is a complex multiple process (for reviews see Hanahan (1988) supra; Bishop (1991) *Cell*, 64:235–248, and Vogelstein and Kinzler (1993), supra). In the fibrosarcoma pathway considered here for exemplary purposes, the first pathological stage, mild fibromatosis, expresses the BPV transgenome at low levels. In the next stage, aggressive fibromatosis, BPV transcription increases, aneuploidy develops (Lindgren et al. (1989) supra), anglogenesis ensues (Kandel et at., (1991) *Cell* 66:1095–1104), and JunB and c-Jun are stimulated, eliciting anchorage independent growth (Bossy-Wetzel et al. (1992) *Genes and Dev.*, 6:2340–2351). In contrast, other transcription factors such as c-Fos, lurid (Bossy-Wetzel et al. (1992) *Genes and Dev.*, 6:2340–2351), SP1, and the basic transcription factors acting on the Rous sarcoma virus promoter remain constant during this tumorigenic process. The present study identifies the intracellular hormone receptors GR and RAR as factors that are specifically up-regulated at the critical fibrosarcoma stage. This differential transcriptional activation is the first molecular parameter that distinguishes the aggressive fibromatosis from the tumor cell, and this transition reflects an important step in the mechanism of fibrosarcoma development.

For clarity, a more detailed analysis of this transition on the GR was performed and is described herein. For example, when pre-neoplastic cells with low GR activity are inoculated into test animals, tumors that arise from those cells display high levels of GR function, consistent with the correlation discovered in this invention, and with the our discovery that a switch in GR activity occurs during tumor progression in vivo. In contrast, mild fibromatosis cells stably transfected with c-Jun and/or JunB are neither tumorigenic nor do they display strong GR transcriptional regulatory activity.

GR is produced and accumulates to the same levels in cells from all four stages of tumorigenesis. Thus, the transition in its activity suggests that some other regulator interacts with GR, either suppressing its activity in the normal and fibromatoses stages, or stimulating its function in the tumor stage. In view of the chromosome rearrangements characteristic of these fibrosarcomas (Lindgren et at., 1989), a suppressor of GR activity might reside on chromosome 14, or a stimulatory factor gene may be on chromosome 8.

A transition in GR transcriptional regulatory activity

The constant level of GR protein throughout tumor development establishes that the GR transition at the tumor stage reflects increased specific activity, not simply increased receptor production. Furthermore, our immunocytochemistry studies demonstrated that GR from all four stages is localized in the cytoplasm in the absence of hormone and translocates efficiently to the nucleus upon hormone treatment. Consistent with that finding, we showed that a constitutively active GR derivative, N556, which lacks the GR hormone binding domain (Miesfeld et aL (1987) *Science*, 236:423–427; Godowski et al. (1987) *Nature*, 325:365–368), is not more active in the pre-neoplastic stages than the hormone-treated full-length GR. Together, these experiments demonstrate that the alteration in GR activity during fibrosarcoma progression must occur after signal transduction events such as hormone entry and metabolism (Funder et al. (1988) *Science*, 242:583–585), GR interaction with Hsp90 (Picard et al. (1990) *EMBO J.*, 6:3333–3340; Bohen et al. (1993) *Proc. Nail Acad. Sci. USA*, 90:11424–11428), hormone binding and nuclear entry.

GR from all four stages in tumorigenesis binds similarly to GRE sequences in vitro. This indicates that the modest GR transcriptional activity observed in normal dermal fibroblasts and fibromatoses reflects a measured capacity of the DNA-bound GR to stimulate the transcription machinery, compared with its robust activity in the fibrosarcoma tumor.

This same transition affects the RAR similarly. However, the effect does not reflect a global transition in transcription factor activity, as expression from other promoters, such as Rous sarcoma virus β-actin, does not change during progression, and SP1 functions in all four stages with comparable efficiency. We conclude that the transition in GR activity at the tumor stage reflects a dramatic and selective increase in the receptor potency for transcriptional enhancement, rather than a change in the efficiency of signal transduction.

Transcriptional regulators may be functionally restricted in normal cells

Tumorigenesis can be considered as one form of cell immortalization, and a progression pathway, such as the fibroblast to fibrosarcoma model examined here, as an ordered series in which the process of immortalization can be investigated. Little is known about what distinguishes normal cells, which have restricted capacities for cell division, from established cultured cell lines, or from cells that have undergone oncogenic transformation. In this context, it is notable that mammalian cells are most often studied biochemically in the context of immortalized cells, which can be readily propagated, cloned and manipulated. Indeed, prior art paradigms for mammalian transcriptional regulatory mechanisms have been established from studies in immortalized cells.

In the case of GR, all previous work suggested that the mere expression of this regulator is sufficient to confer strong transcriptional activation upon promoters bearing linked GREs, and that GR levels limited the magnitude of the activation response. Hence, transfection of mammalian GR into established cell lines from a wide range of tissues and species, including insects (Yoshinaga and Yamamoto (1991) *Molec. Endocrinol.* 5:844–853), fungi (Schena and Yamamoto (1988) *Science,* 241:965–967) and plants (Sehena et al. (1991) *Proc. Natl. Acad. Sci. USA* 88:10421–10425), produced robust regulation upon hormone treatment, and responses that could be amplified further by increasing GR expression. Notably, each study employed immortal cells. Our studies of GR activity in normal and non-immortalized pre-neoplastic cells contrast strongly with those findings: in such cells GR is functional, but confers only modest transcriptional activation (compared to the activity of the same level of receptor at the tumor stage), and overexpression of GR fails to produce increased hormone responsiveness. In addition to the tumor progression pathway, similar conclusions emerged from our comparison of normal and oncogene-transformed mouse embryo fibroblasts, as well as a comparison of normal human keratinocytes with human keratinocytes spontaneously immortalized (containing a mutation in p53) or immortalized with SV40. In every case, only the immortalized cells displayed strong GR activity and dose dependent stimulation by exogenous GR. These findings imply that normal cells and their non-immortalized derivatives may contain a GR modulatory factor, such as an enzymatic activity that modifies both endogenous and exogenously provided receptor protein, or a stoichiometric interacting factor which is generally present in excess.

If this is the case, the same factor would operate on RAR, and its inactivation would release RAR's potent transcriptional regulatory capability. Inactivation of such a factor would be associated with the process that regulates cellular immortalization. An important corollary of our postulate is that normal cells utilize this modulatory factor to restrict the magnitude of transcriptional regulatory signals within some normal "permitted" range. Consistent with this view, many physiological glucocorticoid responses that have been characterized in vivo show modest changes in levels of regulated enzymes, (Hashimoto et al. (1984) *Proc. Natl Acad. Sci. USA,* 81:6637–6641; Poduslo (1989) *Archiv. Biochem. Biophysics,* 272: 318–322). Clearly, the actions of the putative modulatory factor are selective, as not all regulators are affected. Our findings imply that studies of gene regulators carried out using immortalized cells could provide imprecise views of the importance of limiting components, or of the significance of factor interactions and functional communication between factors. This is an important new consideration for investigations that have previously assumed that regulatory phenomena described in established cell lines reflect mechanisms that occur in normal cells.

The significance of the transition in intracellular receptor hormone activities

The relationship between the transition in intracellular hormone receptor activity and dermal fibrosarcoma development is unknown, although the present invention provides clear proof of the correlation. Three possibilities merit consideration: First, the transition might reflect a direct role of the intracellular hormone receptor in tumor progression. For instance, glucocorticoid and retinoic acid receptor activities have been correlated with diverse effects on cell growth and differentiation, and it is possible that increased GR or RAR function drives fibrosarcoma progression. This scheme could be tested by treating mice with agonists or antagonists of these hormones, and examining their effects on tumor development and growth. A second model is that the intracellular hormone receptor transition represents a protective cellular response against tumorigenesis that enhances differentiation so as to counteract hyperproliferation. This "cellular defense" model would explain in part the efficacy of glucocorticoids and retinoids as therapeutic agents in treating certain cancers (for reviews see Kaspers et al. (1994) *Leukemia and Lymphoma* 13:187–201; Smith et al. (1992)*J. Cl. Oncology* 10:839–864). This scheme would also be assessed by pharmacologic studies, e.g., in animals. The third model predicts that intracellular hormone receptors are "bystander" molecules whose transitions to higher activity serve as passive indicators of a key regulatory change in the cell, but that the receptor is not itself directly involved in the mechanism of tumor progression. In all three models, the mechanism by which the intracellular hormone receptor are up-regulated is a key issue. GR is an especially useful tool for such studies because its functional and physical features are well characterized at the level of biochemistry, genetics, and structure, and sensitive assays are available to measure its activities, or those of a putalive intracellular hormone receptor modulatory factor, during tumorigenesis.

EXAMPLES

The following examples are provided by way of illustration only and not by way of limitation. Those of skill will readily recognize a variety of noncritical parameters which could be changed or modified to yield essentially similar results.

Materials and Methods

Unless otherwise specified, the following materials and methods were utilized in performing the Examples below.

Plasmids

The luciferase reporter (de Wet et al. (1987), *Mol. Cell. Biol.* 7:725–737) construct TAT3-Luc contained three tandem GREs derived from the tyrosine aminotransferase (TAT) gene (Jantzen et al. (1987) *Cell,* 49:29–38) located upstream of the minimal alcohol dehydrogenase (Adh) promoter (−33). The AP-1 reporter construct (−73)Col-Lue, contained a fragment of the collagenase promoter (−73) (Angel et al. (1987), *Mol. Cell. Biol.* 7:2256–2266) linked to the lueiferase reporter gene. Three copies of the composite GRE, G(26)A were placed upstream of the Adh promoter to yield G(26)A3-Luc. The R140-Luc reporter construct contains a fragment (124 to +14) of the RARβ2 gene promoter (Vivanco et al, (1991) *EMBO J.* 10:3829–3838). The GR expression vector 6RGR is a SP65-based vector in which the Rous sarcoma virus (RSV) promoter is fused to GR cDNA sequences (Godowski et al. (1988) *Science* 241:812–816). The RAR expression vectors contain the corresponding RARα, βor γ cDNAs cloned into a pSG5 vector (Vivanco et a., 1991). To monitor transfection efficiency the construct 6RZ (β-galactosidase in a 6R background) (Pearce and Yamamoto (1993) *Science* 259:1161–1165) was included in each transfection.

Cell Culture and Transient Transfections

Cultures were established from skin and tumor tissues of several independent BPV transgenic mice (Sippola-Thiele et al., 1989), and maintained in Dulbecco's modified Eagle's medium (DMEM-21, high glucose formulation; Gibco-BRL) containing 8% fetal calf serum (Hyclone). Cells were propagated for no longer than five weeks and always used at low passage number (1–30). Several cultures were tested from each stage of the tumorigenic process: normal fibroblasts, NF (23784, 40950); mild fibromatosis, MF (39614, 14249, 27877); aggressive fibromatosis, AF (BPV7, BPV3, BPV21); fibrosarcoma, FS (BPV1, BPV22, BPV2, BPV11).

Cells were plated at least 12 h before transfeetion at ~0.5×10$^6$ cells per 6 cm dish. Reporter gene DNA (2 μg), together with the 6RZ (100 ng) as an internal control for efficiency of transfection, were introduced into cells using the DEAE-dextran method (Ausubel). Where indicated, the expression vector 6RGR was co-transfected. After exposure to the DNA/DEAE-dextran mixture, the cells were incubated for 24 h in fresh medium containing charcoal-stripped serum (Miesfeld et al., 1987) with or without 100 nM dexamethasone (Sigma). Cells were harvested and the luciferase activity measured according to the instructions of the manufacturer (Promega) and normalized for β-galactosidase expression as previously described (Miner and Yamamoto (1992) *Genes Dev.*, 6:2491–2501). Each experiment was repeated at least six times and the results averaged.

Animal and Tissue Culture of Tumor-Derived Cell Lines

Cultured cells to be injected into nude mice were harvested at subconfluency by trypsinization, washed and resuspended in DMEM without serum. Cells in 0.2 ml of DMEM were injected subcutaneously on the fight flank of 5–6 week old nu/nu male mice (Harlan); animals were inspected for tumors at three day intervals. Tumors to be re-isolated and cultured were excised following cervical dislocation of the animals. The tumors were washed in phosphate buffered saline (PBS) and dissociated in collagenase/dispase (Boehringer-Mannheim; 10 μg/ml for 30 min, at 37° C.). Dissociated cells were then plated and cultured in the same manner as BPV transgenie tumor cell lines.

Immunoblotting

Cells were harvested by centrifugation in 40 mM Tris-HCl (pH 7.8), 10 mM EDTA, 150 mM NaCl, washed in ice-cold PBS, repelleted and frozen in liquid nitrogen. Cells were resuspended in lysis buffer (10 mM HEPES (pH 7.9), 400 mM NaCl, 0.1 mM EGTA, 5% (v/v) glycerol, 1 mM dithiothreitol (DTT) and 1 mM phenylmethyl-sulfonyl fluoride (PMSF)). High-salt extracts were obtained by centrifugation for 30 min at 12 krpm, discarding the pellet; similar results were obtained using extracts from whole cells solubolized with SDS sample buffer (50 mM Tris-Cl (pH 6.8), 100 mM DTT, 2% SDS, 0.1% bromophenol blue, 10% (v/v) glycerol).

Equal amounts of extract protein (5 μg) from each cell stage (NF-40950, MF-14249, AF-BPV3, FS-BPV1) were separated by electrophoresis on a 7.5% SDS-polyacrylamide gel and transferred to an Immobilon membrane (Millipore). Blocking, washing and incubation of the membrane with antibodies were carried out in Tris-buffered saline (TBS, 10 mM Tris-Cl (pH 7.5), 150 mM NaCl) containing 4% nonfat dry milk and 0.05% Tween-20. A mouse monoclonal anti-GR antibody (BUGR2; Gametchu et al. (1984) *Endocrinology*, 114:274–279) was used as primary antibody (1:100, hybridoma cell supernatant), followed by incubation with a secondary (horseradish peroxidase conjugated goat anti-mouse immunoglobulin) antibody (1:31300; Bio-Rad). Protein-antibody complexes were visualized by an enhanced chemiluminescence immunoblotting detection system according to the recommendations of the manufacturer (Amersham).

Immunocytochemistry

Cells were grown in 24-well plates (Corning). The medium was changed to serum-free, phenol-red free DMEM, supplemented with insulin (5 μg/ml) and transferrin (10 μg/ml), with or without 500 nM dexamethasone for 2 h. After three washes with ice-cold PBS, cells were fixed with cold (−20° C.) methanol for 10 min, and then washed with TBS. Nonspecific binding sites were blocked in blocking buffer (BB) (TBS, 1% Triton, 1% glycine, 3% bovine serum albumin and 10% normal goat serum). Fixed cells were treated with a primary rabbit polyclonal anti-GR antibody (PA1-511, 1 μg/ml; Affinity Bioreagents), followed by biotinylated anti-rabbit IgG, and finally horseradish peroxidase, at the dilutions suggested by the manufacturer (ABC, VECTOR laboratories); BB, was used during the antibody incubations, as well as for the washes. Diaminobenzidine (Sigma) was used as a substrate for the peroxidase reaction.

Mobility Shift Assay

Microscale nuclear extracts from dexamethasone treated cells (2 h) were prepared as described by Andrews and Faller (Andrews et al. (1991), *Nucleic Acid Res.*, 19:2499). Briefly, cell pellet was resuspended in Buffer A (10 mM HEPES-KOH (pH 7.9), 1.5 mM MgCl$_2$, 10 mM KCl, 0.5 mM DTT, 0.2 mM PMSF). The cells were allowed to swell on ice for 10 min and vortexed. Samples are centrifuged and the pellet is resuspended in cold Buffer C (20 mM HEPES-KOH (pH 7.9), 25% (v/v) glycerol, 420 mM NaCl, 1.5 mM MgCl$_2$, 0.2 mM EDTA, 0.5 mM DTT, 0.2 mM PMSF) and incubated on ice for 20 min. After centrifugation, the supernatant fraction contained the nuclear extract. Five micrograms of protein from the nuclear extracts were preincubated at room temperature for 15 min in 20 mM HEPES-KOH (pH 7.9), 5 mM MgCl$_2$, 50 mM KCl, 0.1 mM EDTA, 15% (v/v) glycerol, 100 ng poly(dI-dC) and 1 mM DTT. After preincubation, 10$^4$ cpm (3–5 fmol) of the corresponding $^{32}$P-end-labeled synthetic oligonucleotide was added to each reaction and incubated for 20 min at room temperature. Protein-DNA complexes were separated by electrophoresis at 200 V at room temperature through a nondenaturing gel (5% polyacrylamide [29% acrylamide, 1% bisacrylamide]) in 0.5×TBE (89 mM Tris-borate, 2 mM EDTA) running buffer. The gel was dried and exposed overnight using Kodak XAR-5 X-ray film.

The following oligonucleotides were used:
simple GRE-TAT: SEQ.ID NO:1
5'-TCGACTGATCTCGCCAGAACATCATGTTCTGCGT-CGCCAGGC-3',
AP-1(–73)Col: SEQ.ID NO:2
5'-TCGACTCTAGACTGAACGGTGACTCAAACTGCC-GCTGCAGGC-3',
composite GRE-G(26)A: SEQ.ID NO:3
5'TCGACTGATGCCTGTACAGGATGT-FCTAGCTACGAACCCTCGTG AGTCAGTCGAGGC-3'.

To assesss specificity of DNA binding, 50-fold molar excess of unlabeled oligonucleotide (specific (S), same as labeled oligonucleotide), or 200-fold molar excess of a nonspecific oligonucleotide (N, a 35 bp oligonucleotide containing completely unrelated sequences from the polylinker of BlueScript, J. Thomas Ph.D. thesis), were added to the reaction prior to addition of the labeled probe. Where indicated, the anti-GR antibody (BUGR2, 1 µg per reaction; Gametchu et al. (1984) *Endocrinology*, 114:274–279) was added to the reaction also before addition of the labeled probe.

Example 1

GR Activity is Low Before the Fibrosarcoma Stage

To monitor the activity of the endogenous glucocorticoid receptor (GR) during dermal fibroblast tumorigenesis, we performed transient transfection assays using low passage primary cell lines representative of the four stages in this multistep pathway: normal dermal fibroblasts, NF; mild fibromatosis, MF; aggressive fibromatosis, AF; fibrosarcoma, FS. We tested the transcriptional activity of various glucocorticoid response elements (GREs), positioned upstream of a minimal promoter and fused to luciferase reporter sequences (de Wet et al. (1987), *Mol. Cell. Biol.*, 7:725–737); the results were normalized to a co-transfected b-galactosidase expression vector. We first measured the hormone responsiveness of a reporter construct, TAT3-Luc, containing three tandem simple GREs derived from the tyrosine aminotransferase (TAT) gene (Jantzen et al., 1987). Surprisingly, dexamethasone, a synthetic glueocorticoid, evoked only a modest stimulation of the low basal luciferase activity in the NF, MF or AF lines, whereas strong hormonal induction was observed in the FS cells; similar results were obtained using a reporter bearing a different simple GRE (Sakai et al. (1988) *Genes Dev.* 2:1144–1154) derived from the mammary tumor virus LTR. Thus, we conclude that strong endogenous GR activity is observed in the final FS stage cells, but not in the initial three stages of the pathway.

Bossy-Wetzel et al. (Bossy-Wetzel et al. (1992) *Genes and Dev.*, 6:2340–2351) detected substantially more AP-1 DNA binding activity in extracts of the AF and FS cells than in NF or MF cell extracts. To extend these findings, we next tested the transcriptional activity of endogenous AP-1 factors using a luciferase reporter construct bearing an AP-1 response element from the collagenase promoter (-73)Col-Luc (Angel et al. (1987), *Mol. Cell. Biol.*, 7:2256–2266). We found that AP-1 activity was somewhat greater in the AF and FS cells relative to the NF and MF cells from the initial stages. Thus, both GR and AP-1 activities increase in the course of tumor progression, but the stages at which the factors become activated differ.

In view of the observed changes in GR and AP-1 activities, we next tested a composite element that requires both factors for transcriptional activation. The synthetic composite element, G(26)A, which resembles a sequence in the glucocorticoid regulatory region of the glutamine synthetase gene (Zhang and Young (1991) *J. Biol. Chem.*, 266:24332–24338), contains the TAT GRE sequence linked through a 15 bp spacer to the collagenase AP-1 sequence. In this configuration, neither GR alone nor AP-1 alone (either Jun homodimers or Jun-Fos heterodimers) activates a linked reporter gene in transfected embryonal earcinoma F9 cells (which express low levels of endogenous GR and AP-1 factors), whereas co-transfection of GR and AP-1 (Jun-Jun or Jun-Fos) produces a strong synergistic activation upon hormone addition. We transfected a luciferase reporter construct containing three copies of the G(26)A composite element, G(26)A3-Luc, into cell cultures representing each stage of the fibrosarcoma progression. As expected, luciferase activity was dramatically induced by dexamethasone in the tumor cells, supporting the view that GR and AP-1 are both highly active at this stage. However, despite the presence of elevated AP-1 activity in the AF cells, only a modest hormonal induction was conferred through the G(26)A element at this stage.

In contrast to the observed changes in GR and AP-1 activities in these cell cultures, overall transcription levels did not change; the RSV promoter, for example, displayed similar activity in cell lines from all four stages. Similarly, the regulatory factor SP1 activated transcription from the thymidine kinase promoter (–109) to similar levels in all cell lines. We conclude that GR undergoes a selective and striking increase in its capacity to activate transcription, both through simple and composite GREs, at the final stage of fibrosarcoma formation.

Example 2

GR Activity in the AF Stage Correlates with Tumorigenic Potency

Our initial analysis involved representative cell cultures from the four identified stages of the tumorigenesis pathway (NF 40950, MF 14249, AF BPV3, FS BPV1). To assesss the extent of variation among different lines from a given stage, we assayed the activity of GR on the G(26)A composite element in three or more independent cell lines from each stage. We found that all lines derived from normal dermis and mild fibromatoses displayed low GR activity, whereas GR function in all of the fibrosarcoma clones examined was consistently strong. In contrast, aggressive fibromatosis cultures spanned a range of GR activity. Thus, AF BPV7 carried no more GR activity than the MF lines, AF BPV21 contained about 40% of the activity found in a robust FS line, and AF BPV3 displayed an intermediate phenotype.

The observed differences in GR activity among aggressive fibromatosis clones allowed us to test whether GR activity and "tumorigenic strength" might be related. Therefore, we inoculated $10^4$ (or $5 \times 10^5$) cells from each AF cell line and from one representative FS line (BPV1) subcutaneously into nude mice, and monitored formation of tumors. We found that the rate of formation and the relative mass of the tumors were in a rank order: FS-BPV1 > AF-BPV21 ≧ AF-BPV3 > AF-BPV7. Therefore, the differences in GR activity during tumor progression paralleled oncogenic potential.

Example 3

GR is Increased in Tumors Derived from Aggressive Fibromatosis Cells

A prediction of the correlation of GR activity with tumor potential and growth is that GR activity should be high in tumors that arise in mice as a result of progression of inoculated AF stage cells, even if the inoculated cells originally carried only low GR activity. We tested for such a switch in GR function by inoculation into nude mice of AF-BPV3 or AF-BPV21 cells, which have low and intermediate GR activity, respectively; we then assayed dexamethasone responsiveness of the G(26)A composite element in cells from the resultant tumors. All the tumor-derived cell fines displayed high GR activity; similar results were obtained with the simple TAT GRE. Specifically, the AF-BPV3 and AF-BPV21 cells appeared to undergo specific transitions in GR activity, each resulting in tumor cells displaying GR activities comparable to those measured in the bona fide FS-BPV1. As a control, we showed that the GR activity of FS-BPV1 itself was unaffected by the inoculation and rederivation procedure. These results demonstrate that a switch in GR activity occurred in vivo that correlates with the tumor cell transition.

Example 5

GR Protein is Expressed at Similar Levels Throughout Tumor Progression

One mechanism of GR up-regulation would involve increased transcription of the GR gene. To address this possibility, we analyzed GR production and accumulation by immunoblotting of cell extracts from each of the four stages of tumorigenesis. We found that GR protein accumulated to similar levels in NF, MF, AF and FS cells. Thus, the striking increase in GR activity at the fibrosarcoma stage is not due simply to increased production of GR protein. This result shows that either the receptor itself somehow differs when produced in fibrosarcoma cells relative to cells from the prior stages, or that the receptor interacts with a nonreceptor component that modulates GR activity differentially in early stage cells and fibrosarcoma.

Example 6

Transfected GR Fails to Affect GR Activates Characteristic of Each Stage

To test for factors that might suppress GR function in the three initial cell types, we co-transfected a GR expression vector together with a simple GRE reporter, TAT3-Luc, into cell lines representative of each of the four stages. The results revealed that exogenously added GR has no effect on the hormone responsiveness of the NF, MF or AF cultures. At moderate endogenous GR levels, co-transfected GR only slightly increased the magnitude of the dexamethasone response of the FS cells; however, at lower hormone concentrations, we detected increased transcriptional activity with GR co-transfection of the FS cells. In contrast, over a wide range of co-transfected GR expression vector (5 ng to 5 µg), no systematic difference in the overall GR activity was detected in pre-neoplastic stages, except at the highest doses, where a modest reduction in the hormone response was observed. To examine the possibility that the BPV transgene was somehow compromising GR function in normal dermal fibroblasts, we isolated and tested dermal fibroblasts from non-transgenic mice (nNF, or non-transgenic dermal fibroblasts); the same results were obtained, namely a low transcriptional response to dexamethasone and lack of effect of co-transfected GR. In contrast, the same exogenous GR expression vector increased by some 20-fold the level of transcriptional activation by dexamethasone in embryohal carcinoma F9 cells and also markedly up-regulated GR transcriptional activity in HeLa cells. Notably, co-transfected RSV-β-gal produced comparable b-galactosidase levels among F9 cells and the nNF, NF, MF, AF and FS cells, suggesting similar transfection efficiencies. Taken together, these findings imply that the early stage cells suppress GR activity in a manner that cannot be overcome by addition of exogenous GR.

Example 7

GR Undergoes Hormone-Dependent Nuclear Translocation in All Stages

To assesss the nature of the differential GR activity, we examined the ligand-dependent nuclear translocation of GR in normal dermal fibroblasts and the three progressive conditions, MF, AF and FS. In the absence of ligand, GR in monkey kidney fibroblasts (Picard and Yammamoto, 1987) and rat fibroblasts (Qi et al. (1989) *Mol. Endocrinol.* 3:1279–1288) resides predominantly in the cytoplasm, but translocates rapidly to the nucleus upon hormone addition. Consistent with these findings, we found in an immunocytochemical analysis that GR resides in the cytoplasm in the absence of hormone, and is efficiently translocated to the nucleus upon dexamethasone treatment in all four cell stages. We conclude that competence for nuclear localization of GR is not differentially regulated during tumor progression.

Example 8

GR Binds to DNA in Vitro in All Stages of Tumor Development

Another aspect of GR function that might be modulated during tumorigenesis is its recognition and binding of GRE DNA sequences. To examine this possibility, we analyzed by gel mobility shift assays binding to the simple GRE-TAT by GR in nuclear extracts from hormone-treated NF, MF, AF and FS cells. The extracts from the four cell stages were indistinguishable in their GRE binding activities. Incubation with 50-fold excess of the unlabeled GRE oligonucleotide, or 200-fold excess of nonspecific unlabeled oligonucleotide confirmed the specificity of this binding reaction. Moreover, addition of a GR-specific monoclonal antibody to the incubations further retarded the mobility of the DNA-protein complexes, demonstrating that GR is present in the complexes.

We also incubated the four nuclear extracts in the presence of a labeled oligonucleotide containing the collagenase AP-1 site, (−73)Col. As previously shown (Bossy-Wetzel et al. (1992) *Genes and Dev.*, 6:2340–2351), AP-1 DNA binding activity increases during the transition from mild to aggressive fibromatosis cells. Finally, we tested the DNA binding activity of these nuclear extracts to a labeled oligonucleotide containing a composite response element, G(26) A, which confers transcriptional activation only in the presence of both GR and AP-1. In gel retardation assays two major retarded bands were observed. We found that binding to the composite element was increased in the AF extracts, consistent with the increased AP-1 activity in those cells. In each case the binding was specific: a 50-fold excess of the unlabeled composite element abolished binding to the labeled probe, whereas a 200-fold excess of a nonspecific oligonucleotide had no detectable effect.

We conclude from these experiments that GR can bind in vitro to GRE sequences in all cell stages throughout tumorigenesis, and with similar efficiency in the context of a simple GRE, reflecting similar levels of endogenous GR protein. In addition, in the context of a composite element, GR and AP-1 display increased binding activity already at the AF stage, reflecting higher levels of AP-1 protein at that stage. Therefore, differences in DNA binding do not account for the transition in transcriptional activation at the tumor stage.

Example 9

Differential Activity of GR in Normal and Transformed Cells is a General Phenomenon The low level of GR activity detected in the normal and pre-neoplastic dermal fibroblasts was entirely unexpected. We established that this finding was not simply an artifact of the BPV transgene, as normal dermal fibroblasts from non-transgenic mice behaved similarly. Hence, it was possible that normal cells might in general carry only modest GR activity that could not be supplemented by exogenously added receptor, and that the robust and supplementable activities typically observed in established cell lines might reflect systematic and potentially important differences between many normal cells and their transformed counterparts.

To examine this possibility, we extended our studies to a different cell type, embryonic fibroblasts. We compared GR activity in primary mouse embryo fibroblasts with that in embryo fibroblasts transformed by ras and SV40 Large T-antigen. The magnitude of the hormonal induction of luciferase reporter activity was low in the primary embryo cells relative to their transformed derivatives. In addition, co-transfection of increasing concentrations of a GR expression vector did not increase GR activity in the primary cells, whereas it stimulated significantly the hormone response in the transformed embryo fibroblasts. As a co-transfected control, levels of β-gal expression from RSV-β-gal were comparable in the two cell types. Thus, our results with embryonic fibroblasts parallel those with derreal fibroblasts demonstrating a general distinction between intraceHular hormone receptor levels in normal and transformed cells.

Example 10

RAR Activity is Also Low Before the Fibrosarcoma Stage

We established that the observed differential GR transcriptional regulatory activity is not exclusive to fibrosarcoma development. An additional issue was whether this transition in activity was unique to GR. To address this, we tested an evolutionarily distant member of the intracellular receptor supeffamily, the retinoic acid receptor (RAR). We transfected a luciferase reporter construct containing a retinoic acid response element (Vivanco et al., 1991), together with the RSV-β-gal expression vector, into NF, MF, AF and FS cells. RAR displayed substantially higher activity in the tumor cells than in the pre-neoplastic stages. In contrast, the levels of β-galactosidase expression, used as internal control, were comparable within the different stages. As seen with GR, co-transfection of expression vectors encoding RAR α, β or γ, did not increase the hormonal response in the non-tumor stages, whereas a medest stimulation was observed in the co-transfected fibrosarcoma cells. These results suggest that the differential transcriptional activity between normal fibroblasts and fibrosarcoma cells is not an idiosyncrasy of GR, and can be extended to other regulators, at least within the intracellular receptor superfamily.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes as if each were individually indicated to be incorporated by reference for all purposes.

---

What is claimed is:

1. A method of detecting posttranslational regulation of an intracellular hormone receptor in the presence of a cognate hormone, comprising:
  i. transfecting a eukaryotic cell with a recombinant expression cassette which comprises a marker gene operably linked to a promotor with a DNA binding site for the intracellular receptor;
  ii. transfecting an immortal eukaryotic cell with the expression cassette of step (i), wherein the cell of step (i) and the cell of step (ii) express the intracellular receptor in a non rate limiting amount;
  iii. contacting the eukaryotic cell of step (i) and the immortal eukaryotic cell of step (ii) with the cognate hormone;
  iv. measuring the level of expression of the marker gene in the eukaryotic cell of step (i) and the eukaryotic cell of step (ii); and,
  v. comparing the level of expression of the marker gene in the eukaryotic cell of step (i) and the immortal eukaryotic cell of step (ii).

2. The method of claim 1, wherein the eukaryotic cell of step (i) and the immortal eukaryotic cell of step (ii) are mammalian.

3. The method of claim 1, wherein the method after step (ii) further comprises:
  vi. contacting a test cell transformed with the expression cassette of step (i) with a biologically active compound;
  vii. contacting the test cell with the cognate hormone;
  viii. measuring the level of expression of the marker gene in the test cell; and,
  ix. comparing the level of expression of the marker gene in the test cell to the level of expression of the marker gene in the eukaryotic cell of step (i) and the eukaryotic immortal cell of step (ii).

4. The method of claim 1, wherein the eukaryofic cell of step (i) and the immortal eukaryofic cell of step (ii) are transfected with a recombinant intracellular hormone receptor expression cassette comprising a nucleic acid encoding an intracellular hormone receptor operably linked to a promoter.

5. The method of claim 4, wherein the method further comprises:
  (a) contacting a test cell with a biologically active compound, wherein the test cell is transformed with the expression cassette of step (i) and the intracellular hormone receptor expression cassette;
  (b) contacting the cell with the cognate hormone;
  (c) measuring the level of expression of the marker gene; and comparing the level of expression of the marker gene to the level of expression of the marker gene in the cell of step (i) and the cell of step (ii).

6. A method of detecting posttranslational regulation of an intracellular hormone receptor in the presence of a cognate hormone, comprising:
  i. transfecting a eukaryotic cell with a recombinant expression cassette which comprises a marker gene operably linked to a promotor with a DNA binding site for the intracellular receptor;
  ii. transfecting an immortal eukaryotic cell with the expression cassette of step (i), wherein the cell of step (i) and the cell of step (ii) express the intracellular receptor in a non-rate limiting amount;
  iii. contacting the eukaryotic cell of step (i) and the immortal eukaryotic cell of step (ii) with the cognate hormone;
  iv. measuring the level of expression of the marker gene in the eukaryotic cell of step (i) and the eukaryotic cell of step (ii); and,
  v. comparing the level of expression of the marker gene in the eukaryotic cell of step (i) and the immortal eukaryotic cell of step (ii);
wherein the eukaryotic cell of step (i) and the eukaryotic cell of step (ii) are human.

7. A method of detecting posttranslational regulation of an intracellular hormone receptor in the presence of a cognate hormone, comprising:
  i. transfecting a eukaryotic cell with a recombinant expression cassette which comprises a marker gene operably linked to a promotor with a DNA binding site for the intracellular receptor;
  ii. transfecting an immortal eukaryotic cell with the expression cassette of step (i), wherein the cell of step (i) and the cell of step (ii) express the intracellular receptor in a non-rate limiting amount;
  iii. contacting the eukaryotic cell of step (i) and the immortal eukaryotic cell of step (ii) with the cognate hormone;
  iv. measuring the level of expression of the marker gene in the eukaryotic cell of step (i) and the eukaryotic cell of step (ii); and,
  v. comparing the level of expression of the marker gene in the eukaryotic cell of step (i) and the immortal eukaryotic cell of step (ii):

wherein the eukaryotic cell of step (i) and the eukaryotic cell of step (ii) are human skin cells.

8. A method of detecting post translational regulation of an intracellular hormone receptor in the presence of a cognate hormone, comprising:
  i. co-transfecting a first primary cell with
    a. a first expression cassette having a nucleic acid encoding the intracellular hormone receptor operably linked to a first promoter; and,
    b. a second expression cassette having a marker gene operably linked to a second promoter having a response element for the intracellular hormone receptor;
  ii. transfecting a second cell with the second expression cassette;
  iii. separately contacting the first primary cell and the second cell with the cognate hormone;
  iv. measuring the expression of the marker gene from the first primary cell and the second cell; and,
  v. comparing the expression of the marker gene from the first primary cell and the second cell.

9. The method of claim 8, wherein the first primary cell and the second cell are of the same cell type.

10. The method of claim 8, wherein the first primary cell is a mammalian cell.

11. The method of claim 8, wherein the method further compriies:
  vi. transfecting an immortal cell line with the first expression cassette and the second expression cassette of step (i);
  vii. measuring the level of expression of the marker gene expressed by the transfected immortal cell line; and,
  viii. comparing the level of expression of the marker gene from the first primary cell and the second cell to the immortal cell line.

12. A method of detecting posttranslational regulation of an intracellular hormone receptor in the presence of a cognate hormone, comprising:
  i. co-transfecting a first primary cell with
    a. a first expression cassette having a nucleic acid encoding the intracellular hormone receptor operably linked to a first promoter; and,
    b. a second expression cassette having a marker gene operably linked to a second promoter having a response element for the intracellular hormone receptor;
  ii. transfecting a second cell with the second expression cassette;
  iii. separately contacting the first primary cell and the second cell with the cognate hormone;
  iv. measuring the expression of the marker gene from the first primary cell and the second cell; and,
  v. comparing the expression of the marker gene from the first primary cell and the second cell;
wherein the first primary cell is a human skin cell grown from a tissue sample without serial passage in culture.

13. A method of detecting posttranslational regulation of an intracellular hormone receptor in the presence of a cognate hormone, comprising:
  i. co-transfecting a first primary cell with
    a. first expression cassette having a nucleic acid encoding the intracellular hormone receptor operably linked to a first promoter: and,
    b. a second expression cassette having a marker gene operably linked to a second promoter having a response element for the intracellular hormone receptor:
  ii. transfecting a second cell with the second expression cassette;
  iii. separately contacting the first primary cell and the second cell with the cognate hormone;
  iv. measuring the expression of the marker gene from the first primary cell and the second cell; and,
  v. comparing the expression of the marker gene from the first primary cell and the second cell;
  vi. transfecting an immortal cell line with the first expression cassette and the second expression cassette of step (i);
  vii. measuring the level of expression of the marker gene expressed by the transfected immortal cell line; and,
  viii. comparing the level of expression of the marker gene from the first primary cell and the second cell to the immortal cell line;
wherein the first primary cell and the second primary cell are human skin cells, and the immortalized cell line is an immortalized skin cell line.

14. A method of detecting posttranslational regulation of an intracellular hormone receptor in the presence of a cognate hormone, comprising:
  i. co-transfecting a first primary cell with
    a. a first expression cassette having a nucleic acid encoding the intracellular hormone receptor operably linked to a first promoter; and,
    b. a second expression cassette having a marker gene operably linked to a second promoter having a response element for the intracellular hormone receptor;
  ii. transfecting a second cell with the second expression cassette;
  iii. separately contacting the first primary cell and the second cell with the cognate hormone;
  iv. measuring the expression of the marker gene from the first primary cell and the second cell and,
  v. comparing the expression of the marker gene from the first primary cell and the second cell;
  vi. transfecting an immortal cell line with the first expression cassette and the second expression cassette of step (i);
  vii. measuring the level of expression of the marker gene expressed by the transfected immortal cell line; and,
  viii. comparing the level of expression of the marker gene from the first primary cell and the second cell to the immortal cell line.
wherein the level of expression of marker gene in the second cell relative to the level of expression of the marker gene in the first primary cell and the immortal cell line indicates whether the second cell is a fibrosarcoma.

15. A method of identifying a compound which differentially modulates posttranslational activity of an intracellular hormone receptor in an immortal cell compared to a primary cell, comprising:
  (i) transfecting the primary cell, which expresses the intracellular hormone in a non rate limiting mount, with an expression cassette comprising a marker gene operably linked to a promoter, wherein the promoter comprises an intracellular hormone response element;
  (ii) transfecting the immortal cell with an expression cassette comprising a marker gene operably linked to a promoter, wherein the promoter comprises an intracellular hormone response element;
  (iii) contacting the primary cell and the immortal cell with a non rate limiting mount of cognate hormone;

(iv) measuring the level of expression of the marker gene in the primary cell and the immortal cell;

(v) contacting the primary cell and the immortal cell with the test compound;

(vi) measuring the level of expression of the marker gene in the primary cell and the immortal cell; and, (vii) comparing the level of expression of the marker gene in the primary cell and the immortal cell in step (iv) and step (vi).

16. The method of claim 15, wherein the primary cell of step (i) and the immortal cell of step (ii) are transfected with an expression cassette comprising a nucleic acid which encodes the intracellular receptor.

17. A method of identifying a compound which differentially modulates activity of an intracellular hormone receptor in an immortal cell compared to a primary cell, comprising:

(i) transfecting the primary cell, which expresses the intracellular hormone in a non-rate limiting amount, with an expression cassette comprising a marker gene operably linked to a promoter, wherein the promoter comprises an intracellular hormone response element;

(ii) transfecting the immortal cell with an expression cassette comprising a marker gene operably linked to a promoter, wherein the promoter comprises an intracellular hormone response element:

(iii) contacting the primary cell and the immortal cell with a non-rate limiting amount of cognate hormone;

(iv) measuring the level of expression of the marker gene in the primary cell and the immortal cell;

(v) contacting the primary cell and the immortal cell with the test compound;

(vi) measuring the level of expression of the marker gene in the primary cell and the immortal cell; and, (vii) comparing the level of expression of the marker gene in the primary cell and the immortal cell in step (iv) and step (vi);

wherein the primary cell of step (i) and the immortal cell of step (ii) are human skin cells.

18. A kit for the detection of posttranslational regulation of intracellular hormone receptor activity, comprising a container and an expression cassette encoding a marker gene operably linked to a promoter, wherein the promoter comprises an intracellular hormone response element, and wherein the promoter alters expression of the marker gene upon binding of the intracellular hormone receptor response element to an intracellular hormone receptor.

19. The kit of claim 18, wherein the kit further comprises a second expression cassette which encodes an intracellular hormone receptor.

20. The kit of claim 18, wherein the kit further comprises a second expression cassette which encodes an intracellular hormone receptor, an immortal cell fine, normal cells, and instructional materials.

* * * * *